(12) United States Patent
Lee et al.

(10) Patent No.: US 7,393,644 B2
(45) Date of Patent: Jul. 1, 2008

(54) METHOD FOR REAL-TIME DETECTION OF POLYMERASE CHAIN REACTION

(75) Inventors: Young-sun Lee, Seongnam-si (KR); Young-a Kim, Suwon-si (KR); Sang-hyo Kim, Yongin-si (KR); Jae-jeong Kim, Seoul (KR); Kak Namkoong, Seoul (KR); Hee-kyun Lim, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 404 days.

(21) Appl. No.: 11/049,316

(22) Filed: Feb. 2, 2005

(65) Prior Publication Data

US 2005/0181405 A1 Aug. 18, 2005

(30) Foreign Application Priority Data

Feb. 14, 2004 (KR) .................... 10-2004-0009841

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search ............... None
See application file for complete search history.

(56) References Cited

U.S. PATENT DOCUMENTS 6,306,584 B1 * 10/2001 Bamdad ................ 435/6
7,135,294 B2 * 11/2006 Lee et al. ................ 435/6
2002/0072054 A1   6/2002 Miles et al. ............ 435/6

FOREIGN PATENT DOCUMENTS

WO    WO 01/42508    *  6/2001

OTHER PUBLICATIONS

Notice to Submit Response for Application No. 10-2004-0009841 (English and Foreign Version).

* cited by examiner

*Primary Examiner*—Teresa E Strzelecka
(74) *Attorney, Agent, or Firm*—Cantor Colburn LLP (57) ABSTRACT

A method for real-time detection of polymerase chain reaction (PCR) is provided. The method includes: manufacturing a reactor having a plurality of electrodes; immobilizing a PCR primer to surfaces of electrodes; injecting a mixture for a PCR into the reactor to perform the PCR on the surfaces of electrodes and measuring an impedance of the PCR product.

11 Claims, 10 Drawing Sheets

FIG. 10B

METHOD FOR REAL-TIME DETECTION OF POLYMERASE CHAIN REACTION

BACKGROUND OF THE INVENTION

This application claims the priority of Korean Patent Application No. 10-2004-0009841, filed on Feb. 14, 2004, in the Korean Intellectual Property Office, the disclosure of which is incorporated herein in its entirety by reference.

1. Field of the Invention

The present invention relates to a method for real-time detection of polymerase chain reaction (PCR), and more particularly, to a method for detecting whether or not PCR is proceeding well by measuring in real-time the impedance change of PCR products as PCR is proceeding.

2. Description of the Related Art

Polymerase chain reaction (PCR) is method of amplifying DNA, for example it may include mixing DNA samples, polymerase and deoxyribose Nucleoside TriPhosphate (dNTP), adjusting the temperature of the mixture appropriately and amplifying the DNA.

The conventional PCR detection employs gel electrophoresis to show only the qualitative result of the amplified DNA after PCR is finished, and has many problems including an accuracy problem in quantitative detection of DNA. To solve this, real-time PCR devices have been developed, which enables the quantitative analysis of DNA by detecting the magnitude of fluorescence that is in proportion to concentration of amplified DNA, through an optical detection system.

So far, real-time PCR chips need a variety of optical apparatuses such as laser sources, micro mirrors, microscopes, and filters, and at the same, expensive fluorescent dye is used. In addition, for the purpose of using less samples and quickly performing analysis as well as decrease reduction in size of devices, PCR chips using a micro-electro-mechanical system (MEMS) have been developed. However, the real-time PCR chips have a problem in reducing the size in case of fluorescent detection, and an economic problem in case of using MEMS.

As another example of the conventional real-time PCR chip detection, there is a method for measuring impedance while PCR is proceeding in a solution. Theoretically, if PCR is performed in a solution, the impedance should show a sequential tendency as the PCR product increases. However, actually, a variety of materials are mixed such that it is difficult to find the tendency in relation to the PCR product. In addition, when the impedance is measured, as time passes by, the measured signal of the PCR product decreases due to non-singular adhesion of components of PCR samples other than DNA, for example, enzymes or PCR reaction buffers, in which the components are adhered to electrodes. Accordingly, the result according to the PCR cycle lacks repeatability. Also, due to the non-singular adhesion, change occurs on the surfaces of electrodes such that it is difficult to measure the PCR product itself generated in the solution.

SUMMARY OF THE INVENTION

The present invention provides a method by which a reactor having various types of electrodes is manufactured; a polymerase chain reaction (PCR) primer is immobilized to electrodes and then a PCR mixture is injected inside the reactor; and while solid PCR, in which PCR proceeds on the surfaces of electrodes, is performed, impedance is measured in real time to determine whether PCR is proceeding well.

According to an aspect of the present invention, there is provided a polymerase chain reaction detection method including: manufacturing a reactor having a plurality of electrodes; immobilizing a polymerase chain reaction primer to surfaces of electrodes; and injecting a mixture for a polymerase chain reaction into the reactor to perform the PCR on the surfaces of electrodes and measuring an impedance of the polymerase chain reaction product.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
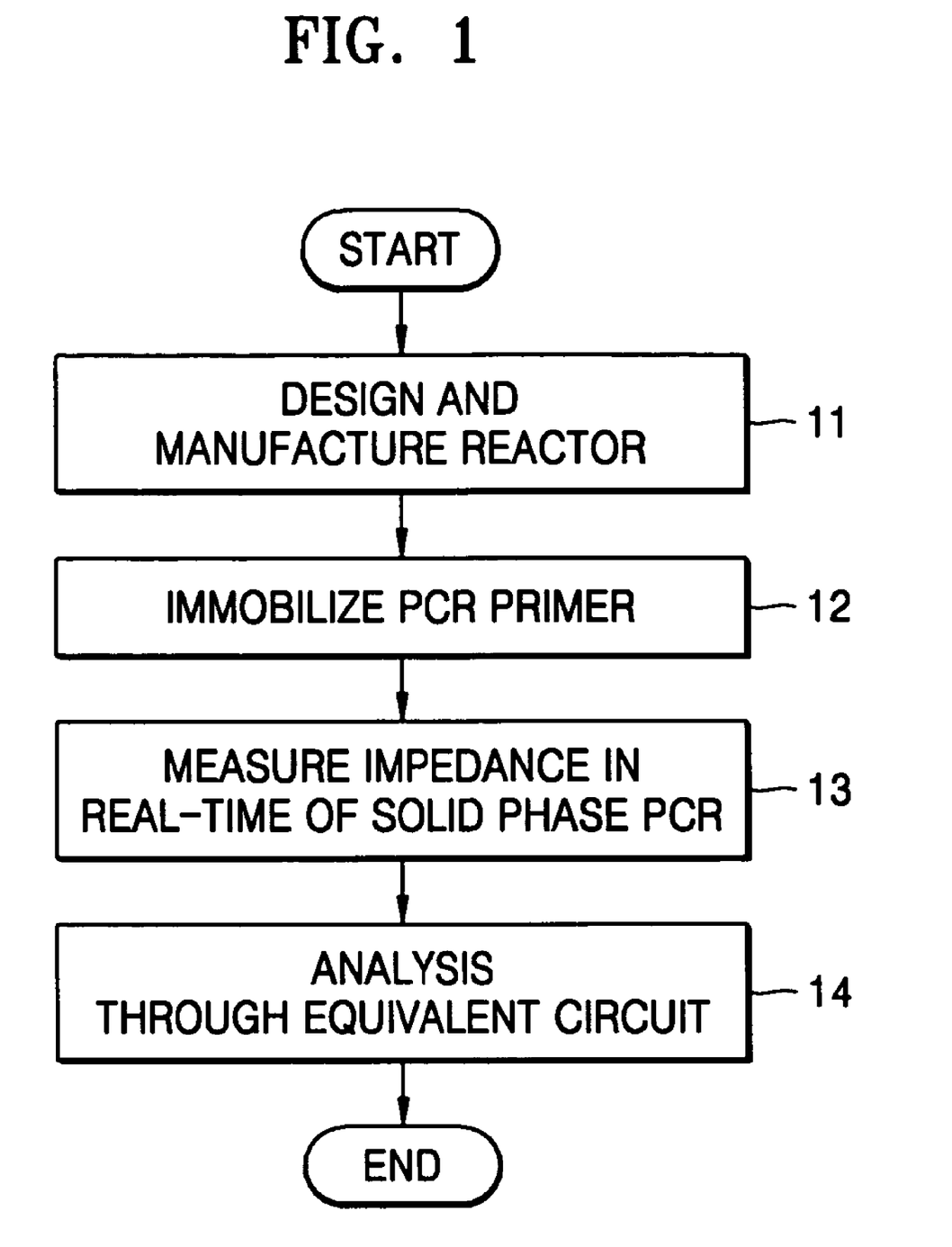
FIG. 1 is a flowchart of a method for real-time detection of PCR according to the present invention.

Referring to the flowchart of FIG. 1 showing a method for real-time detection of PCR according to the present invention, first, a reactor having an electrode structure to be used in the present invention is designed and manufactured in step 11. The reactor is a micro PCR chip. For this, electrodes to be used are patterned on a glass substrate. Materials to be used as the electrodes are sputtered and then lifted off. On another glass substrate, reaction chambers are etched and then, inlets and outlets are formed by using sandblast. The manufactured two glass substrates are fusion-bonded such that a predetermined amount of a PCR mixture solution can flow into the inside of the chip. The electrode structure can be designed in a variety of ways by modifying an interval between electrodes, a number of electrodes, a shape of each electrode, an area of each electrode, etc.

Figure 2:
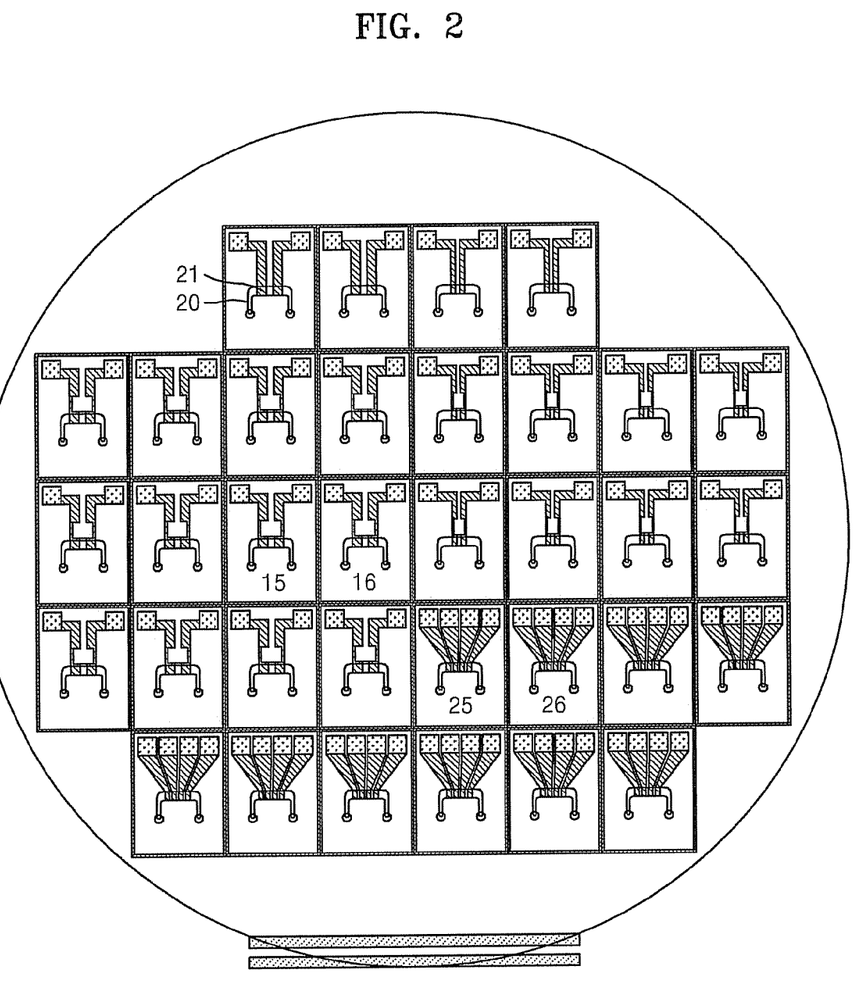
FIG. 2 illustrates a micro PCR chip having 17 pairs of different electrode structures.

In the present embodiment, as shown in FIG. 2, a micro PCR chip having 17 pairs of different electrode structures is manufactured. Reference number 20 indicates a reaction chamber in a PCR chip into which a PCR mixture is injected, and reference number 21 indicates an electrode located in the reaction chamber 20. Among this variety of electrode structures, according to conditions such as composition of the PCR mixture, a kind of a buffer, and salt content, an appropriate electrode structure is selected. A reference number written inside a chip represent the chip number.

Next, a PCR primer is immobilized in step 12. In the present embodiment, solid PCR is performed in order to enable to read impedance change with a high sensitivity. The solid PCR means that the PCR is proceeding on surface of an electrode. For this, the PCR primer should be immobilized to the surface of the electrode. First, a PCR primer is synthesized, which is introduced a chemical group bound well to the electrode according to a kind of electrode material. Materials with high conductivity such as gold or platinum are desirable for the electrode materials. In the present embodiment, gold is used. The synthesized PCR primer is solved in a buffer to be injected into a reaction chamber, and then is immobilized through using a reaction such as a self assembled monolayer (SAM) reaction. At this time, in the primer to be immobilized, any one type of an upstream and a downstream may be immobilized, or both can be immobilized. In the present embodiment, immobilization is performed by using an upstream primer in which the chemical group is replaced with a sulfhydryl group that has a good reactivity to the electrode material.

Next, impedance of the solid PCR is measured in real time in step 13. Into the reactor in which the primer is immobilized, a PCR mixture including a PCR buffer, dNTP, $MgCL_2$ and Taq. polymerase enzyme, is injected. While proceeding temperature cycles appropriate to the PCR, an impedance signal is measured at an extension temperature in each cycle. Here, the impedance signal is not only measured in each cycle but can also be measured after all of the cycles are completed.

Figure 3A:
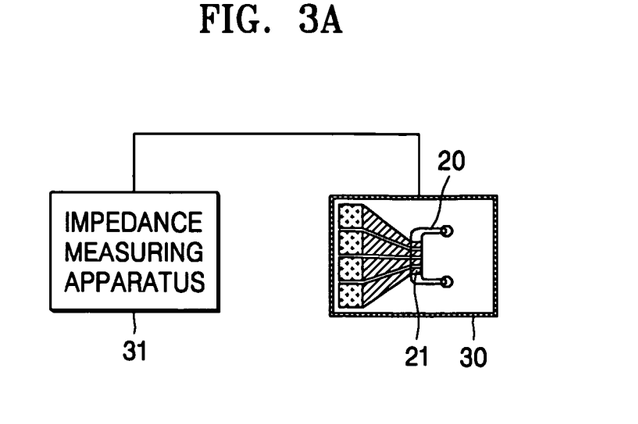
FIG. 3A illustrates that the impedance of a micro PCR chip is measured using an impedance measuring apparatus.
Figure 3B:
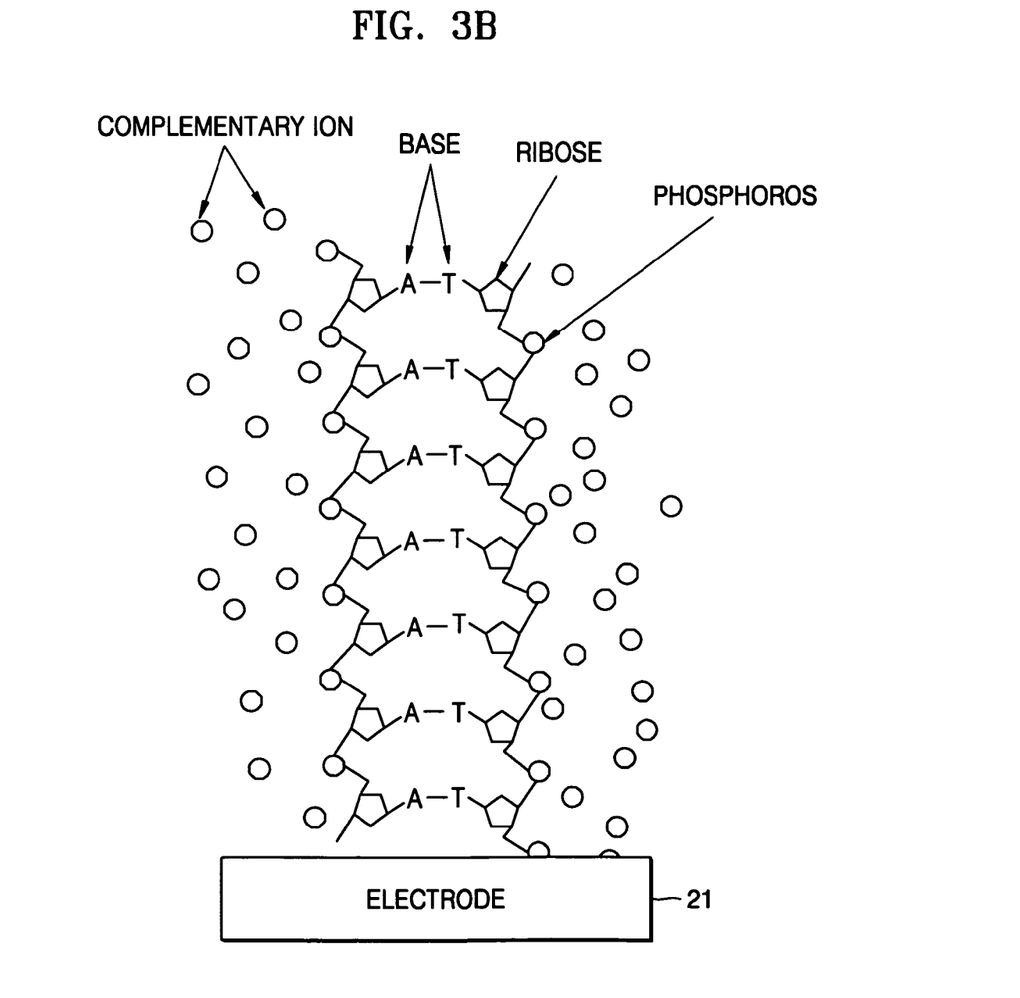
FIG. 3B illustrates that an oligonucleotide is bound to an electrode.

FIG. 3A illustrates that the impedance of a micro PCR chip is measured by using an impedance measuring apparatus 31. Reference number 30 indicates a micro PCR chip. FIG. 3B illustrates that an oligonucleotide is bound to an electrode 21.

Figure 4A:
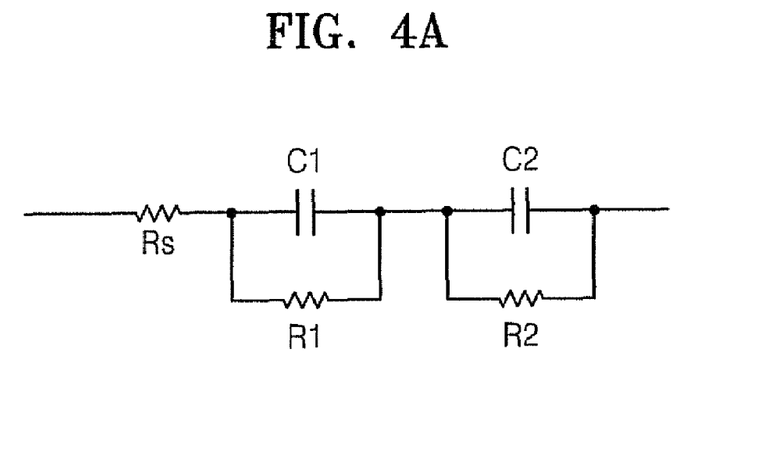
FIG. 4A illustrates an impedance equivalent circuit of a PCR mixture.

FIG. 4A illustrates an impedance equivalent circuit of a PCR mixture. Referring to FIG. 4A, $R_s$ denotes a resistance of the mixture, $R_1$ denotes a resistance between the mixture and the electrode, $C_1$ denotes a capacitance between the mixture and the electrode, $R_2$ denotes a resistance on the surface of the electrode, and $C_2$ denotes a capacitance on a surface of the electrode. Impedance of the equivalent circuit of FIG. 4A can be calculated as the following equations 1:

$$Z = R_s + [R_1^{-1} + j\omega C_1]^{-1} + [R_2^{-1} + j\omega C_2]^{-1}$$

$$Z' = R_s + R_1/[1+\omega^2 R_1^2 C_1^2] + R_2/[1+\omega^2 R_2^2 C_2^2]$$

$$Z'' = -\omega R_1^2 C_1/[1+\omega^2 R_1^2 C_1^2] - \omega R_2^2 C_2/[1+\omega^2 R_2^2 C_2^2]$$

Figure 4B:
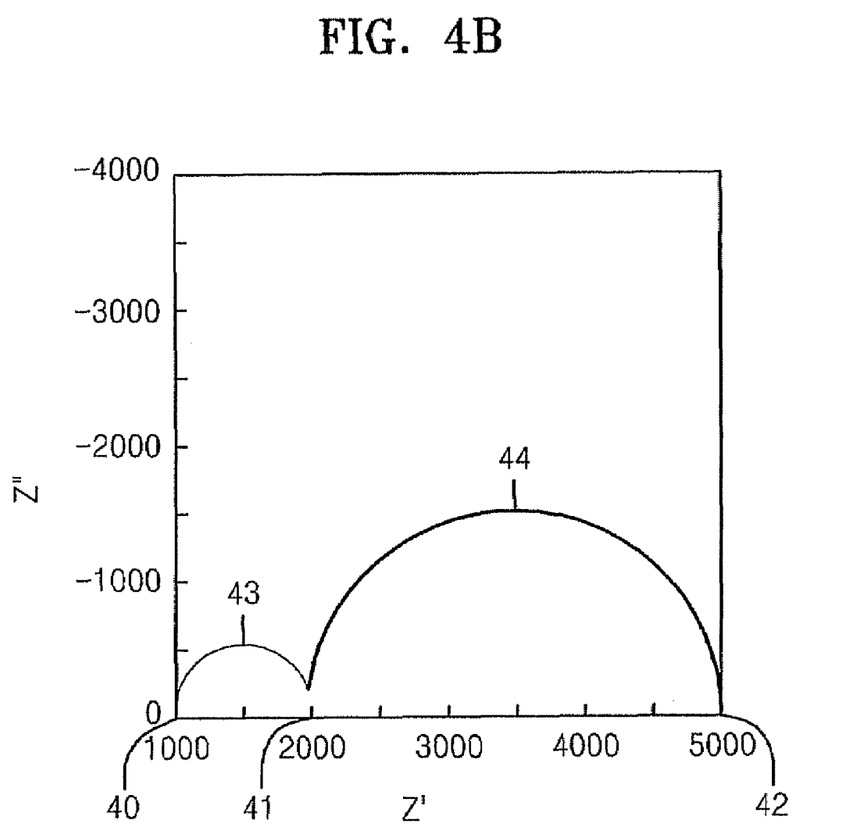
FIG. 4B is a Nyquist plot expressing an imaginary component with respect to a real component of an impedance calculated according to the equivalent circuit of FIG. 4A.

Here, Z' denotes a real component of Z, and Z" denotes an imaginary component of Z. If the impedance is measured, the analysis of the measured impedance through the equivalent circuit can be performed in step 14. The analysis, for example, can be performed to find which PCR proceeds more strongly, by using a Nyquist plot of the imaginary component with respect to the real component of the impedance calculated in the equation 1, as shown in FIG. 4B. That is, it can be learned which reaction is the strongest among in the mixture, between the mixture and the electrode, and on the surface of the electrode. In FIG. 4B, reference number 40 indicates a location of $R_s$, reference number 41 indicates a location of $R_s + R_1$, and reference number 42 indicates a location of $R_s + R_1 + R_2$. A radius of a semicircle of reference number 43 is $R_1/2$, and that of reference number 44 is $R_2/2$. Referring to FIG. 4B, shapes can vary with respect to values of $R_{1\ and\ R2}$. Accordingly, in order to enable easier impedance measuring, gene amplification can be confirmed by making a surface effect stronger through the solid PCR.

Figure 5A:
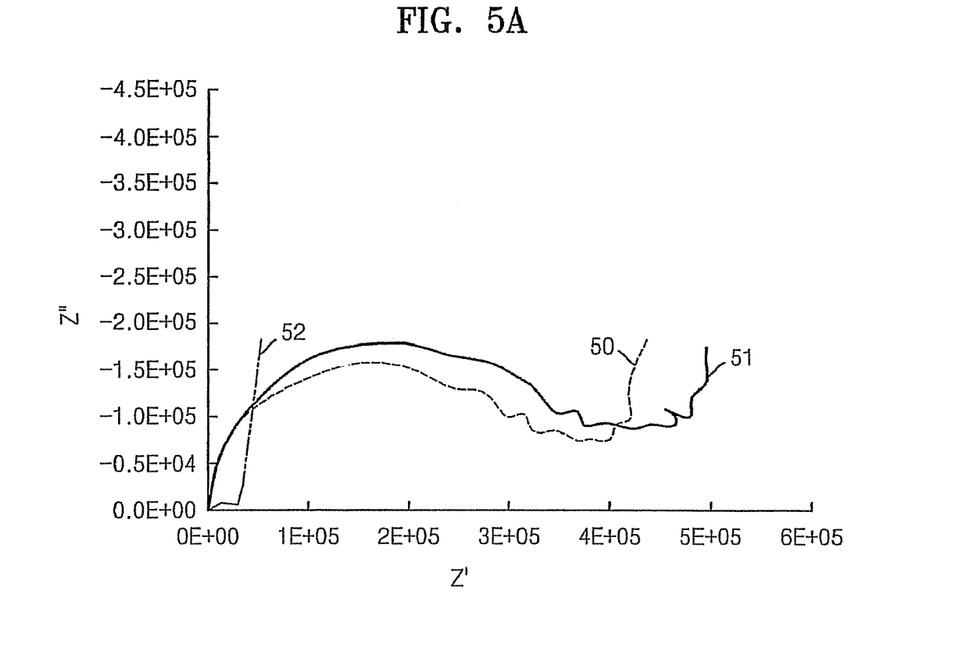
FIGS. 5A and 5B illustrates change in an imaginary component with respect to a real component of impedance measured with respect to hybridization in PCR chips 25 and 26 of FIG. 2.
Figure 5B:
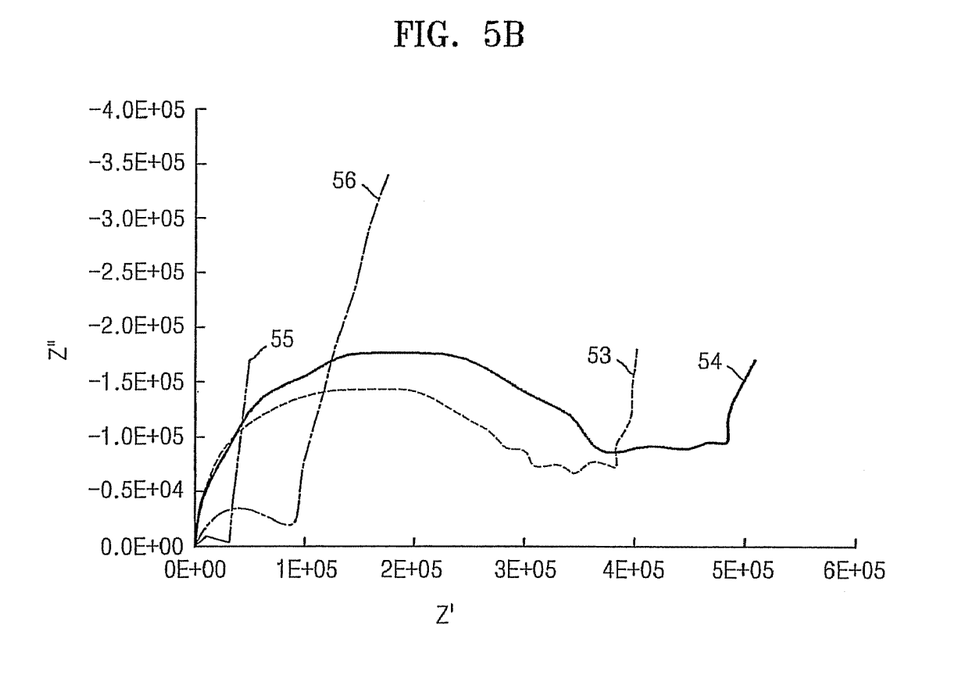
Figure 6A:
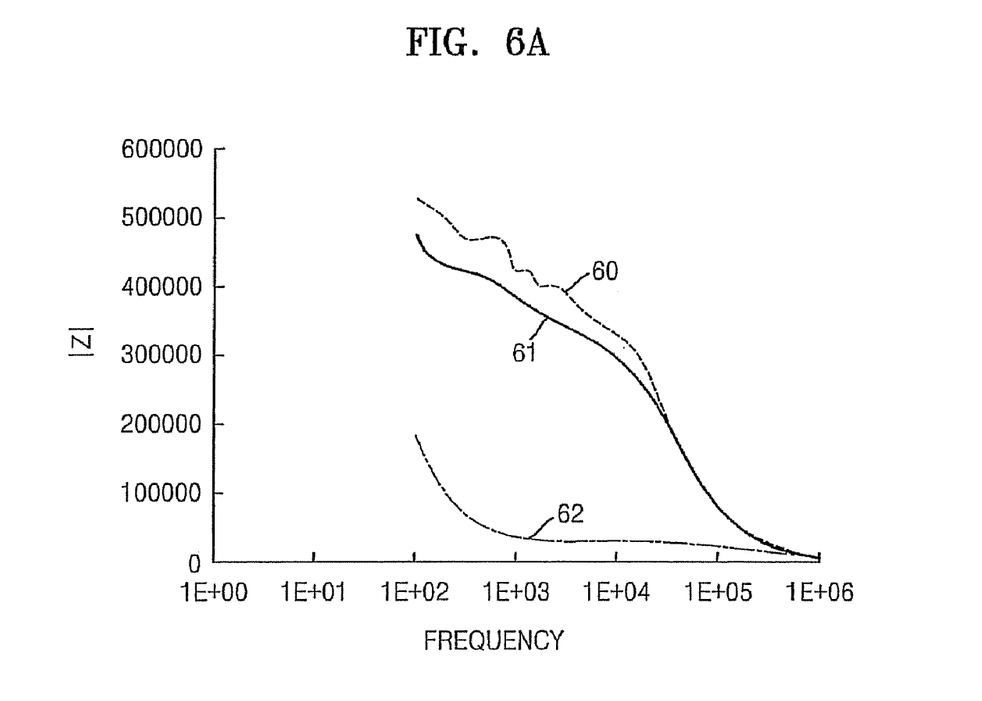
FIGS. 6A and 6B are showing the impedance of FIGS. 5A and 5B as the magnitude of impedance with respect to frequency.
Figure 6B:
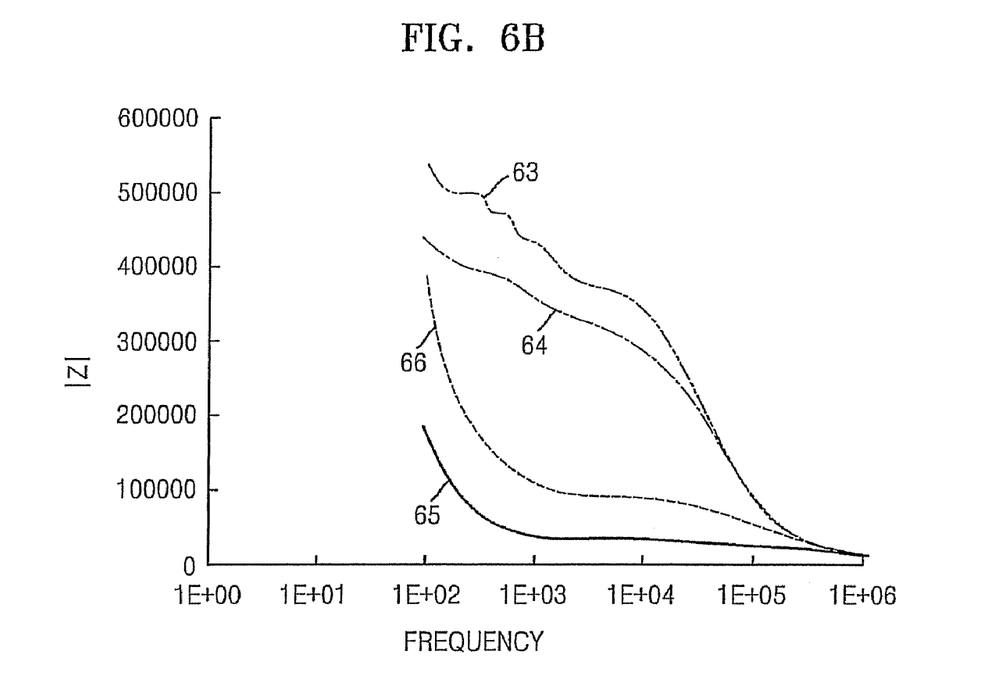
Figure 7A:
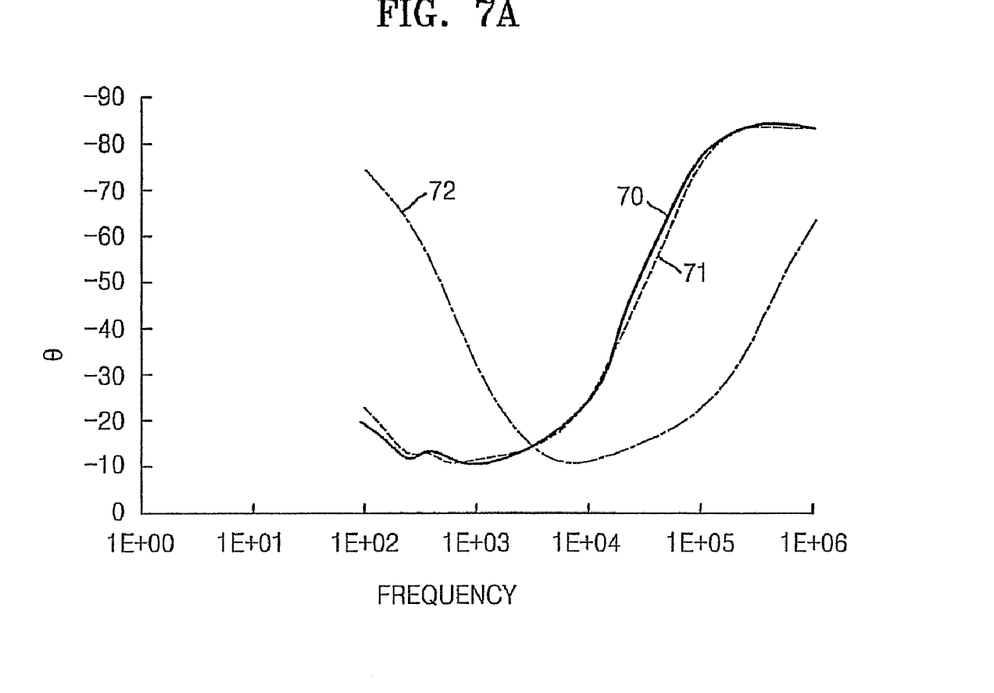
FIGS. 7A and 7B are showing the impedance of FIGS. 5A and 5B as the phase of impedance with respect to frequency.
Figure 7B:
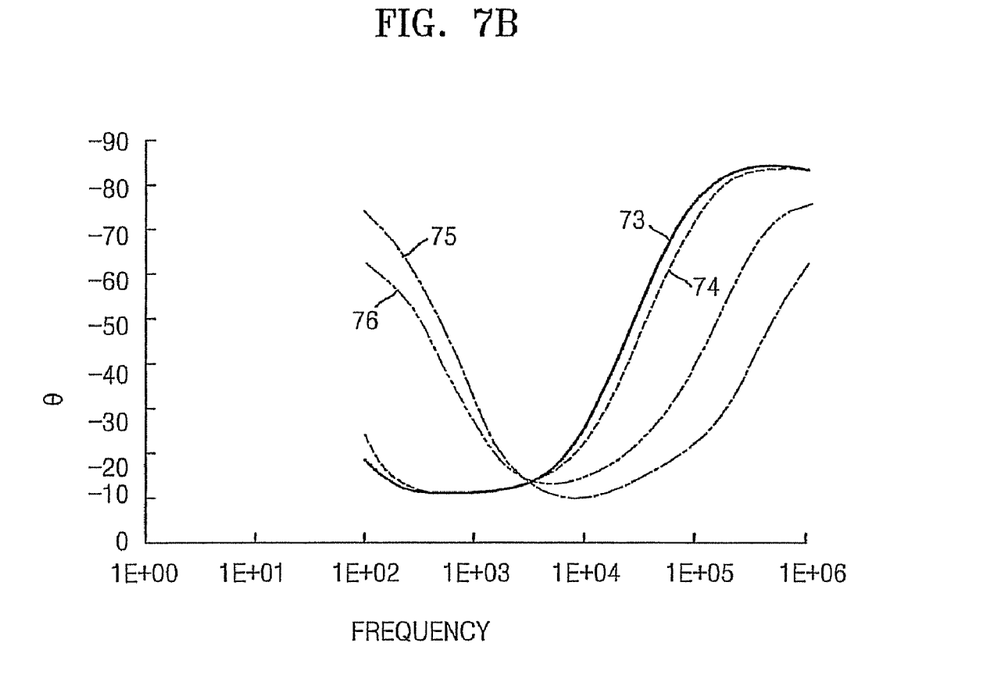

FIGS. 5 through 7 show impedance changes with respect to hybridization in PCR chips 25 and 26 of FIG. 2. FIGS. 5A, 6A, and 7A show the impedance changes when a linker is immobilized to an electrode, while FIGS. 5B, 6B, and 7B show the impedance changes when the primer is immobilized to an electrode.

More specifically, FIGS. 5A and 5B show change in Z" in relation to Z' in the equation 1. Hybridization times are 1 minute, 5 minutes, 30 minutes, and 1 hour, respectively. In the two graphs, reference numbers 50 and 53 indicate impedances measured before the linker and the primer, respectively, are immobilized to an electrode. Reference numbers 51 and 54 are impedances measured after the linker and the primer, respectively, are immobilized. Referring to FIGS. 5A and 5B, there are differences in impedances before and after immobilization of the linker and the primer. Accordingly, it can be seen that the linker and the primer are well immobilized to the electrode. Meanwhile, with regard to the results of measuring impedances with respect to the hybridization, reference number 52 indicates the result when the linker is immobilized, and shows that there is no impedance change due to the hybridization even after an hour. When the primer is immobilized to the electrode and the hybridization proceeds for 30 minutes, there is no change as indicated by reference number 55. However, when the hybridization proceeds for an hour, an impedance change is measured as indicated by reference number 56 such that it can be seen that gene is amplified.

FIGS. 6A and 6B show magnitudes of impedances, respectively, with respect to frequency. Reference numbers 60 and 63 indicate measured values before the linker and the primer, respectively, are immobilized to an electrode, and reference numbers 61 and 64 indicate measured values after the linker and the primer, respectively, are immobilized to an electrode. Reference number 62 indicates measured values in case that the hybridization proceeds for a minute, 5 minutes, 30 minutes, and an hour, when the linker is immobilized. According to the graph, there is no change in measured values. In case that the primer is immobilized, reference number 65 indicates measured values on the hybridization for 30 minutes, and reference number 66 on the hybridization for an hour. According to the graph, it can be seen that change in the magnitude of the impedance is measured and accordingly, that gene is amplified.

FIGS. 7A and 7B show phases of impedances, respectively, with respect to frequency. Reference numbers 70 and 73 indicate measured values before the linker and the primer, respectively, are immobilized to an electrode, and reference numbers 71 and 74 indicate measured values after the linker and the primer, respectively, are immobilized to an electrode. Reference number 72 indicates measured values in case that the hybridization proceeds for a minute, 5 minutes, 30 minutes, and an hour, when the linker is immobilized. In case that the primer is immobilized, reference number 75 indicates measured values on the hybridization for 30 minutes, and reference number 76 indicates measured values on the hybridization for an hour. It can be seen that change in the phases of the impedance is measured and accordingly, that gene is amplified.

According to FIGS. 5 through 7, any one among the magnitude of the imaginary component with respect to the real component of the impedance, the magnitude with respect to frequency, and the phase with respect to frequency, can show whether the gene is amplified.

Figure 8A:
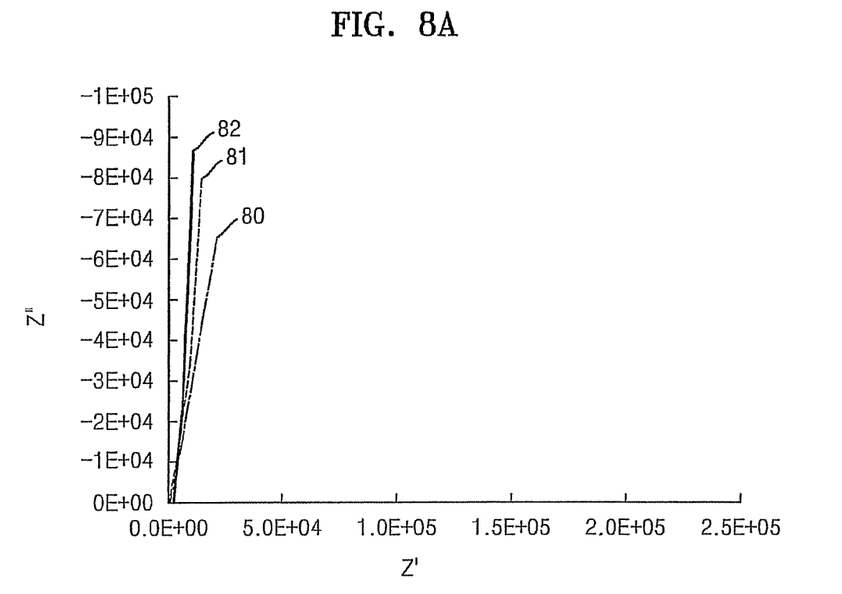
FIGS. 8A and 8B illustrates change in an imaginary component with respect to a real component of impedance measured with respect to annealing cycle in PCR chips 15 and 16 of FIG. 2.
Figure 8B:
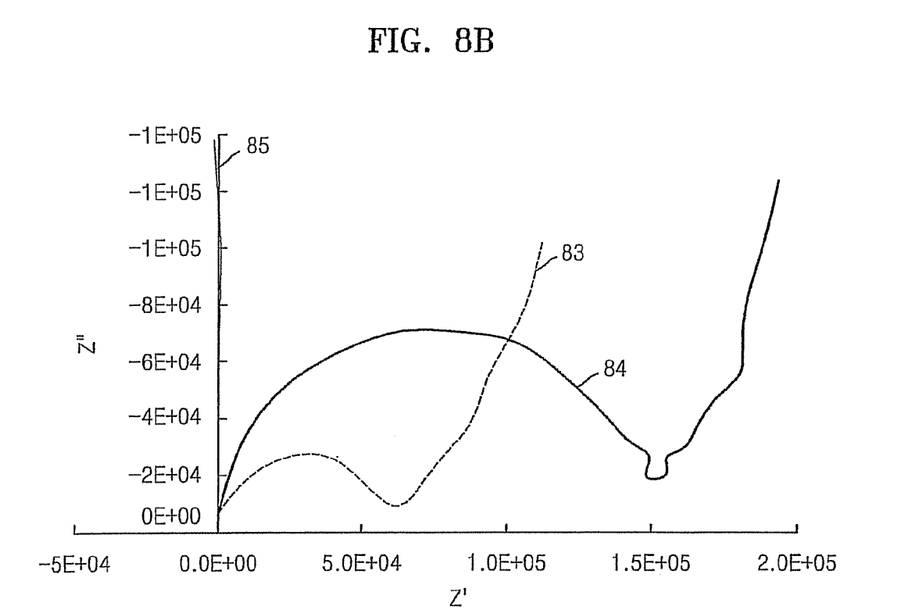
Figure 9A:
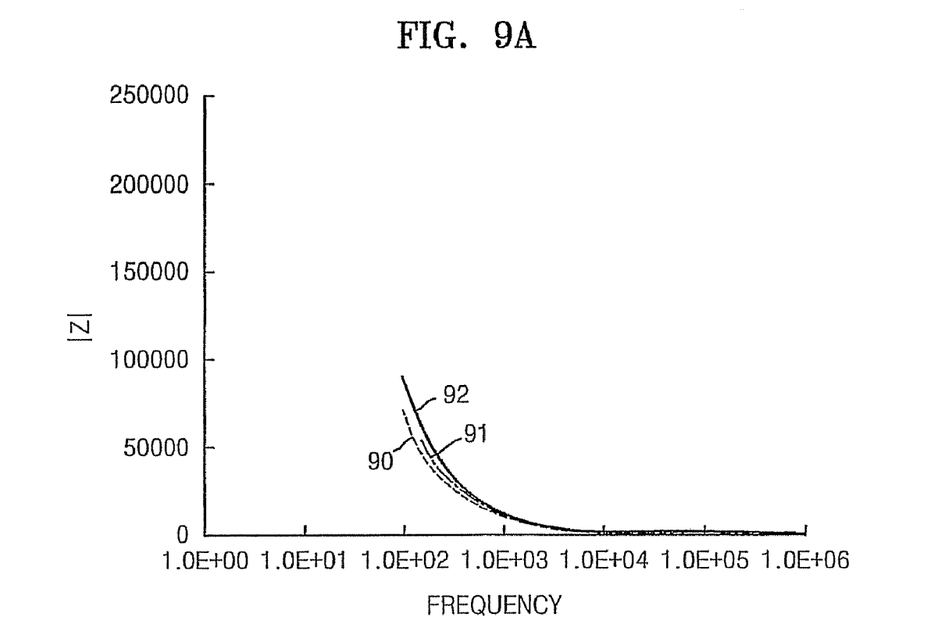
FIGS. 9A and 9B are showing the impedance of FIGS. 8A and 8B as the magnitude of impedance with respect to frequency.
Figure 9B:
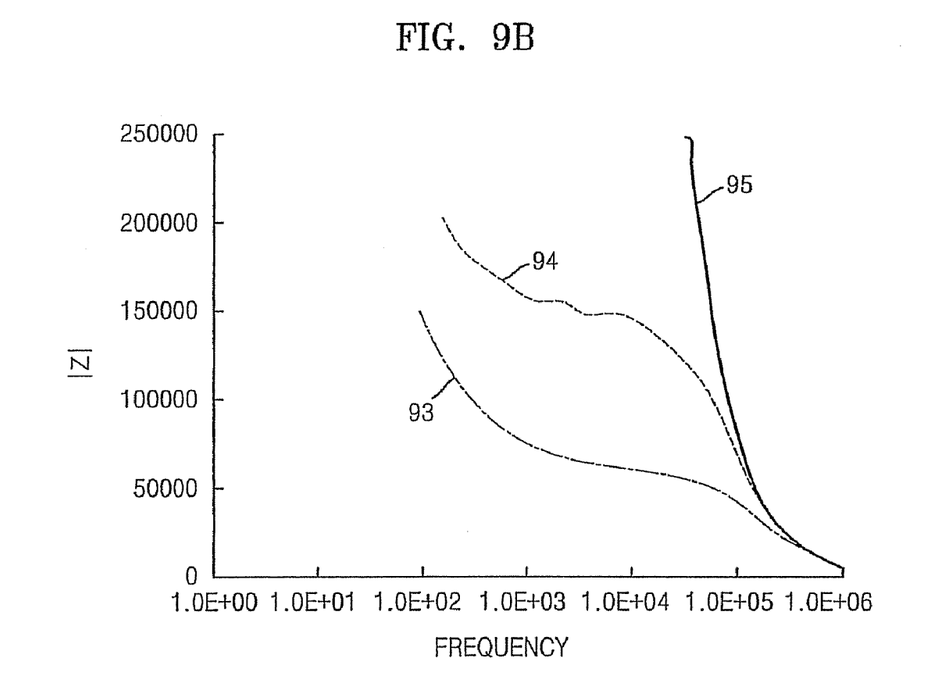
Figure 10A:
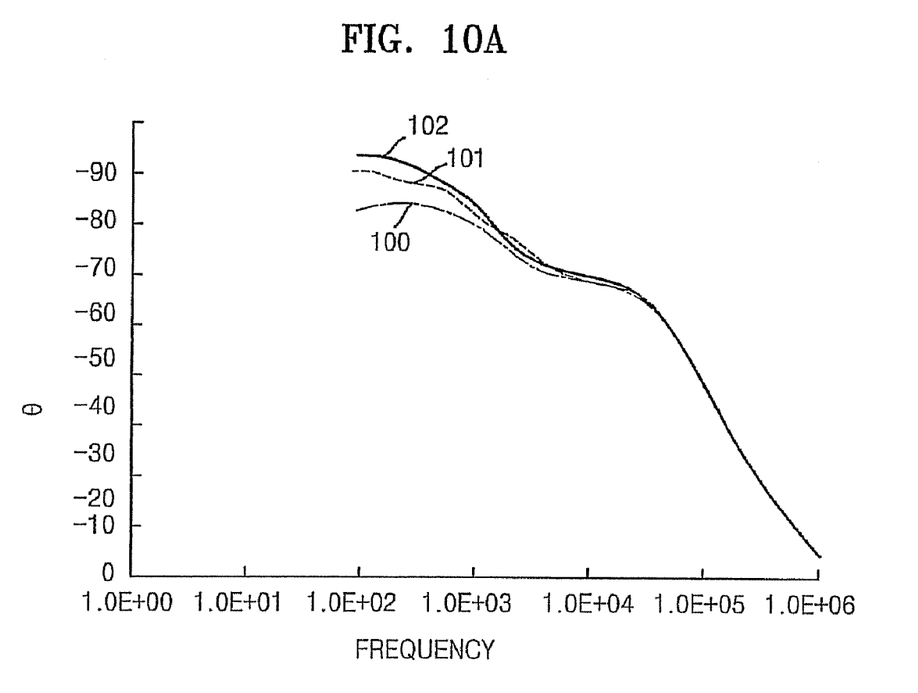
FIGS. 10A and 10B are showing the impedance of FIGS. 8A and 8B as the phase of impedance with respect to frequency.
Figure 10B:
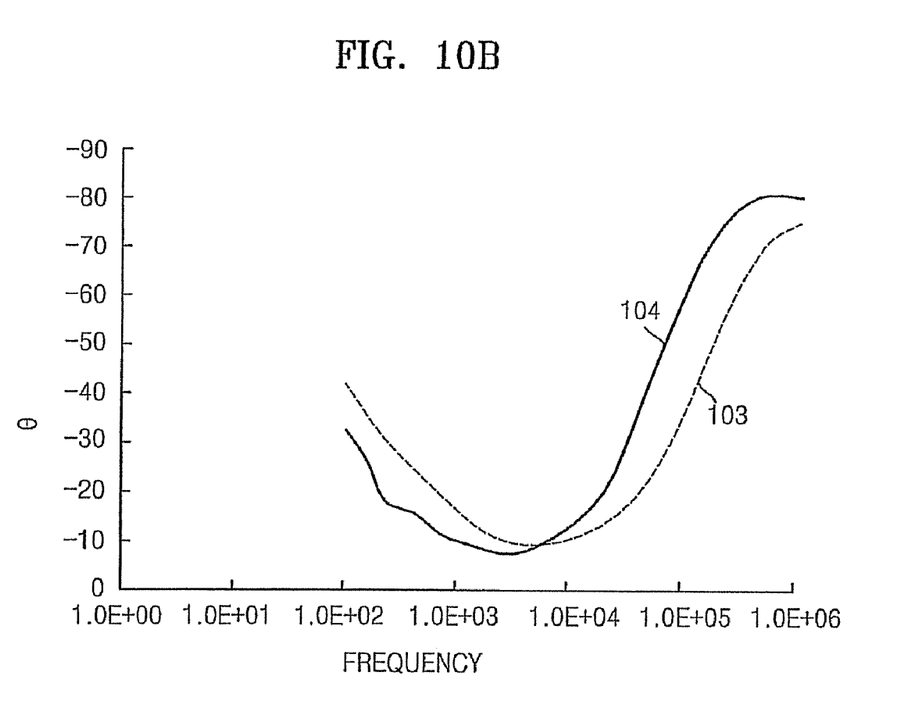

FIGS. 8 through 10 show values obtained by measuring solid PCR in chips 15 and 16 among the chips shown in FIG. 2. An object gene of PCR is that of a Hepatitis B virus (HBV). FIGS. 8A, 9A, and 10A show the measured values when a linker is immobilized to an electrode, while FIGS. 8B, 9B, and 1B show the measured values when a primer is immobilized to an electrode.

FIGS. 8A and 8B show change in Z" with respect to Z' in the equation 1 while annealing processes of 1, 20, and 40 cycles, respectively, are performed. When the linker is immobilized, there is little change in the measured impedances in FIG. 8A. When the primer is immobilized, however, the changes in the measured values are great enough to show that the gene is amplified.

FIGS. 9A and 9B show magnitudes of impedances, respectively, with respect to frequency. Reference numbers 90 and 93 indicate measured values, respectively, when 1 cycle annealing is performed, reference numbers 91 and 94 indicate measured values, respectively, when 20 cycle annealing is performed, and reference numbers 92 and 95 indicate measured values, respectively, when 40 cycle annealing is performed.

FIGS. 10A and 10B show phases of impedances, respectively, with respect to frequency. Reference numbers 100 and 103 indicate measured values, respectively, when 1 cycle annealing is performed, reference numbers 101 and 104 indicate measured values, respectively, when 20 cycle annealing is performed, and reference numbers 102 indicates measured values when 40 cycle annealing is performed.

According to the graphs, as in FIGS. 8A and 8B, when the linker is immobilized, there is little change in the measured values. When the primer is immobilized, however, the changes in the measured values are great with increasing frequency of the annealing cycles, and accordingly, it can be seen that the gene is amplified.

According to the present invention, while solid PCR is performed, the impedance is measured such that the sensitivity can be improved better than the measuring in the solution. In addition, the non-singular adhesion to the surface of an electrode can be removed such that measuring the PCR product in real time with high repeatability is enabled.

What is claimed is:

1. A method for detecting a polymerase chain reaction, the method comprising:
   providing a reactor including a plurality of electrodes;
   immobilizing a polymerase chain reaction primer to each of the plurality of electrodes; and
   injecting a polymerase chain reaction mixture into the reactor;
   measuring an impedance in the polymerase chain reaction mixture;
   measuring an impedance between the mixture and at least one of the plurality of electrodes;
   measuring an impedance on a surface of the at least one of the plurality of electrodes;
   detecting the presence of a polymerase chain reaction based on the measured impedances.

2. The method of claim 1, wherein the step of providing the reactor comprises:
   providing an electrode structure having a plurality of electrode characteristics;
   patterning electrodes according to the electrode structure on a first glass substrate;
   etching reaction chambers on a second substrate; and
   fusion-bonding the first and second substrates.

3. The method of claim 2, wherein the electrode structure is gold, platinum or a combination thereof.

4. The method of claim 1, wherein the immobilizing the polymerase chain reaction primer comprises:
   synthesizing the polymerase chain reaction primer by introducing a predetermined material to be bound to the plurality of electrodes;
   solving the synthesized polymerase chain reaction primer in a buffer to make a polymerase chain reaction primer mixture; and
   injecting the polymerase chain reaction primer mixture inside the reactor and immobilizing the polymerase chain reaction primer mixture to the electrode.

5. The method of claim 4, wherein the predetermined material is a chemical of the sulfhydryl group.

6. The method of claim 4, wherein the polymerase chain reaction primer mixture is immobilized to the plurality of electrodes by a self assembled monolayer reaction.

7. The method of claim 4, wherein in the polymerase chain reaction primer is an upstream primer, a downstream primer, or a combination thereof.

8. The method of claim 1, further comprising:
   determining a location within the reactor where the reaction is performed strongest by analyzing the measured impedance; and
   adjusting polymerase chain reaction conditions of the reactor in order that the polymerase chain reaction is performed relatively more strongly in a location where the reaction is performed strongest.

9. The method of claim 8, wherein the measured impedance is selected from a group consisting of a magnitude of an imaginary component with respect to a real component of the impedance, a magnitude of the impedance with respect to frequency, and a phase of the impedance with respect to frequency.

10. The method of claim 2, wherein the plurality of electrode characteristics includes variations in individual electrode shapes, individual electrode areas and intervals between adjacent electrodes.

11. The method of claim 2, wherein the first and second substrates comprise glass.

* * * * *